US00PP28144P2

(12) United States Plant Patent
Verschoor

(10) Patent No.: US PP28,144 P2
(45) Date of Patent: Jun. 27, 2017

(54) ***PHLOX* PLANT NAMED 'VERSRED'**

(50) Latin Name: *Phlox paniculata*
Varietal Denomination: Versred

(71) Applicant: Adrianus Verschoor, Haarlem (NL)

(72) Inventor: Adrianus Verschoor, Haarlem (NL)

( * ) Notice: Subject to any disclaimer, the term of this patent is extended or adjusted under 35 U.S.C. 154(b) by 35 days.

(21) Appl. No.: 14/998,432

(22) Filed: Dec. 31, 2015

(51) Int. Cl.
*A01H 5/02* (2006.01)

(52) U.S. Cl.
USPC ..... Plt./320

(58) Field of Classification Search
USPC ..... Plt./320
See application file for complete search history.

*Primary Examiner* — Anne Grunberg
(74) *Attorney, Agent, or Firm* — C. A. Whealy

(57) ABSTRACT

A new and distinct cultivar of *Phlox* plant named 'Versred', characterized by its broadly upright and relatively compact plant habit; freely flowering habit; large inflorescences with cherry red-colored flowers; long flowering period; good garden performance; and relative tolerance to Powdery Mildew.

2 Drawing Sheets

Botanical designation: *Phlox paniculata.*
Cultivar denomination: 'VERSRED'.

BACKGROUND OF THE INVENTION

The present invention relates to a new and distinct cultivar of *Phlox* plant, botanically known as *Phlox paniculata* and hereinafter referred to by the name 'Versred'.

The new *Phlox* plant is a product of a planned breeding program conducted by the Inventor in Haarlem, The Netherlands. The objective of the breeding program was to create new compact and freely-flowering *Phlox* plants with attractive flower colors.

The new *Phlox* plant originated from an open-pollination in Haarlem, The Netherlands, of an unnamed selection of *Phlox paniculata* as the female, or seed, parent, not patented with an unknown selection of *Phlox paniculata* as the male, or pollen, parent. The new *Phlox* plant was discovered and selected by the Inventor as a single flowering plant from within the progeny of the stated open-pollination in a controlled environment in Haarlem, The Netherlands in July, 2012.

Asexual reproduction of the new *Phlox* plant by cuttings in a controlled environment in Haarlem, The Netherlands since August, 2012 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Versred'. These characteristics in combination distinguish 'Versred' as a new and distinct *Phlox* plant:

1. Broadly upright and relatively compact plant habit.
2. Freely flowering habit.
3. Large inflorescences with cherry red-colored flowers.
4. Long flowering period.
5. Good garden performance.
6. Relative tolerance to Powdery Mildew.

Plants of the new *Phlox* and the female parent selection differ primarily in the following characteristics:

1. Plants of the new *Phlox* are shorter and more compact than plants of the female parent selection.
2. Flowers of plants of the new *Phlox* are more intense red in color than flowers of plants of the female parent selection.
3. Plants of the new *Phlox* are healthier, stronger and more tolerant to Powdery Mildew than plants of the female parent selection.

Plants of the new *Phlox* can be compared to plants of *Phlox paniculata* 'Starfire', not patented. In side-by-side comparisons conducted in Haarlem, The Netherlands, plants of the new *Phlox* and 'Starfire' differed in the following characteristics:

1. Plants of the new *Phlox* were shorter and more compact than plants of 'Starfire'.
2. Plants of the new *Phlox* were more freely flowering than plants of 'Starfire'.
3. Plants of the new *Phlox* were healthier, stronger and more tolerant to Powdery Mildew than plants of 'Starfire'.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of typical flowering plants of 'Versred' grown in a container.

The photograph on the second sheet is a close-up view of a typical inflorescence of 'Versred'.

DETAILED BOTANICAL DESCRIPTION

The aforementioned photographs and following observations, measurements and values describe plants grown during the spring, summer and autumn in 1.5-liter containers and ground beds in an outdoor nursery in Haarlem, The Netherlands and under cultural practices typical of commercial *Phlox* production. During the production of the plants, day temperatures ranged from 14° C. to 30° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: *Phlox paniculata* 'Versred'.

Parentage:

*Female, or seed, parent*.—Unnamed selection of *Phlox paniculata*, not patented.

*Male, or pollen, parent*.—Unknown selection of *Phlox paniculata*, not patented.

Propagation:

*Type*.—By cuttings.

*Time to initiate roots, summer*.—About three weeks at temperatures about 20° C.

*Time to produce a rooted plant, summer*.—About six weeks at temperatures about 20° C.

*Root description*.—Fine, fibrous.

*Rooting habit*.—Freely branching; medium density.

Plant description:

*Plant and growth habit*.—Herbaceous perennial; broadly upright and relatively compact plant habit; overall shape, broadly obovate; low vigor.

*Plant height*.—About 33.5 cm.

*Plant width* (*spread*).—About 24.3 cm.

*Lateral branches*.—Length: About 18.5 cm. Diameter: About 4 mm. Internode length: About 2.4 cm. Strength: Strong. Aspect: Upright to about 55° from vertical. Texture: Smooth, glabrous. Luster: Slightly glossy. Color: Close to 146A moderately to strongly tinged with close to between N77B and N186C.

Leaf description:

*Arrangement*.—Opposite, simple.

*Length*.—About 7.9 cm.

*Width*.—About 2.8 cm.

*Shape*.—Elliptic to ovate; very slightly carinate.

*Apex*.—Apiculate.

*Base*.—Obtuse to truncate.

*Margin*.—Entire; very finely serrate, inconspicious; very slightly revolute.

*Texture, upper and lower surfaces*.—Smooth, glabrous.

*Luster, upper surface*.—Slightly glossy.

*Luster, lower surface*.—Matte.

*Venation pattern*.—Pinnate.

*Color*.—Developing leaves, upper surface: Close to 143A. Developing leaves, lower surface: Close to between 143B and 144A. Fully expanded leaves, upper surface: Close to NN137A; venation, close to 143C. Fully expanded leaves, lower surface: Close to 138B; venation, close to 144B to 144C.

*Petioles*.—Length: About 2 mm. Diameter: About 2 mm by 4 mm. Texture, upper and lower surfaces: Smooth, glabrous. Color, upper surface: Close to 144B strongly tinged with close to N186B. Color, lower surface: Close to 144C.

Flower description:

*Flower type and flowering habit*.—Single rotate and salverform flowers arranged in compound terminal panicles; flowers face upright to outwardly; panicles roughly pyramidal in shape; freely flowering habit with about 100 flowers developing per inflorescence.

*Fragrance*.—Moderately fragrant; sweet, pleasant.

*Natural flowering season*.—Plants begin flowering about nine months after planting; long flowering period, plants flower continuously from July through September in The Netherlands.

*Flower longevity*.—Flowers last about ten days on the plant; flowers not persistent.

*Flower buds*.—Height: About 1.9 cm. Diameter: About 4 mm. Shape: Oblanceolate. Color: Close to N74C; immature tube, close to 147D with longitudinal stripes, close to N77C; immature calyx, close to 144C tinged with close to N186A, most prominently towards the apex.

*Inflorescence height*.—About 13.8 cm.

*Inflorescence diameter*.—About 12.6 cm.

*Flower diameter*.—About 3.2 cm.

*Flower depth*.—About 2.5 cm.

*Petals*.—Quantity per flower: Typically five in a single whorl; petals fused at the base into a narrow tube; free parts slightly imbricate. Length: About 3.7 cm; lower 2.1 cm fused. Lobe width: About 1.7 cm. Shape: Free part, spatulate. Apex: Obtuse. Margin: Entire. Texture, upper surface: Smooth, glabrous; velvety. Texture, lower surface: Smooth, glabrous. Luster, upper surface: Matte. Luster, lower surface: Slightly glossy. Color: When opening, upper surface: Close to between 53C and 58B; towards the throat, close to N74A; throat, close to N79B to N79C. When opening, lower surface: Close to 67D flushed with close to 70A to 70B; tube, close to N79B. Fully opened, upper surface: Close to between N57A and 58B; towards the throat, close to N74A; throat, close to N79B to N79C. With development, color becomes closer to between 53C and N57A; towards the throat, close to N74A; and throat, close to N79B to N79C. Fully opened, lower surface: Close to 67D flushed with close to 70A to 70B; tube, close to N77B.

*Sepals*.—Quantity per flower: Typically five in a single whorl, fused towards the base; calyx, campanulate. Length: About 8 mm. Width: About 1.25 mm. Shape: Lanceolate. Apex: Narrowly apiculate. Margin: Entire. Texture, upper and lower surfaces: Smooth, glabrous. Luster, upper and lower surfaces: Matte. Color: When opening, upper surface: Close to 144C slightly tinged with close to N186A, most prominently towards the apex. When opening, lower surface: Close to 144C tinged with close to N186A, most prominently towards the apex. Fully opened, upper surface: Close to 146D slightly tinged with close to N186A, most prominently towards the apex. Fully opened, lower surface: Close to 146C tinged with close to N186A, most prominently towards the apex.

*Peduncles*.—Length, primary peduncles: About 9.7 cm. Diameter, primary peduncles: About 2 mm. Length, secondary peduncles: About 4 cm. Diameter, secondary peduncles: About 1.25 mm. Aspect, primary peduncles: Erect. Aspect, secondary peduncles: About 55° from vertical. Strength: Strong. Texture: Smooth, glabrous. Color: Close to 146C to 146D; upper surface strongly tinged with close to N200A.

*Pedicels*.—Length: About 5 mm. Diameter: About 1 mm. Angle: About 45° from the peduncle axis. Strength: Strong. Texture: Smooth, glabrous. Color: Close to 144B; upper surface strongly tinged with close to N200A.

*Reproductive organs*.—Stamens: Quantity per flower: Typically five; filaments fused with petals. Filament length: About 0.5 mm. Filament color: Close to 155A. Anther length: About 2 mm. Anther shape: Oblong; basifixed. Anther color: Close to 195C. Pollen amount: Moderate. Pollen color: Close to 4D. Pistils: Quantity per flower: One. Pistil length: About 1.9 cm. Stigma shape: Cleft, three-parted. Stigma color: Close to 150D. Style length: About 1.8 cm. Style color: Close to N77C. Ovary color: Close to 143B.

*Seeds and fruits*.—Seed and fruit development have not been observed on plants of the new *Phlox*.

Garden performance: Plants of the new *Phlox* have been observed to have good garden performance and tolerate rain, wind, high temperatures about 35° C. and to be winter hardy to USDA Hardiness Zone 6.

Disease & pest resistance: Plants of the new *Phlox* have been observed to be relatively tolerant to Powdery Mildew; plants of the new *Phlox* have not been observed to be resistant to pests and other pathogens common to *Phlox* plants.

It is claimed:

1. A new and distinct *Phlox* plant named 'Versred' as illustrated and described.

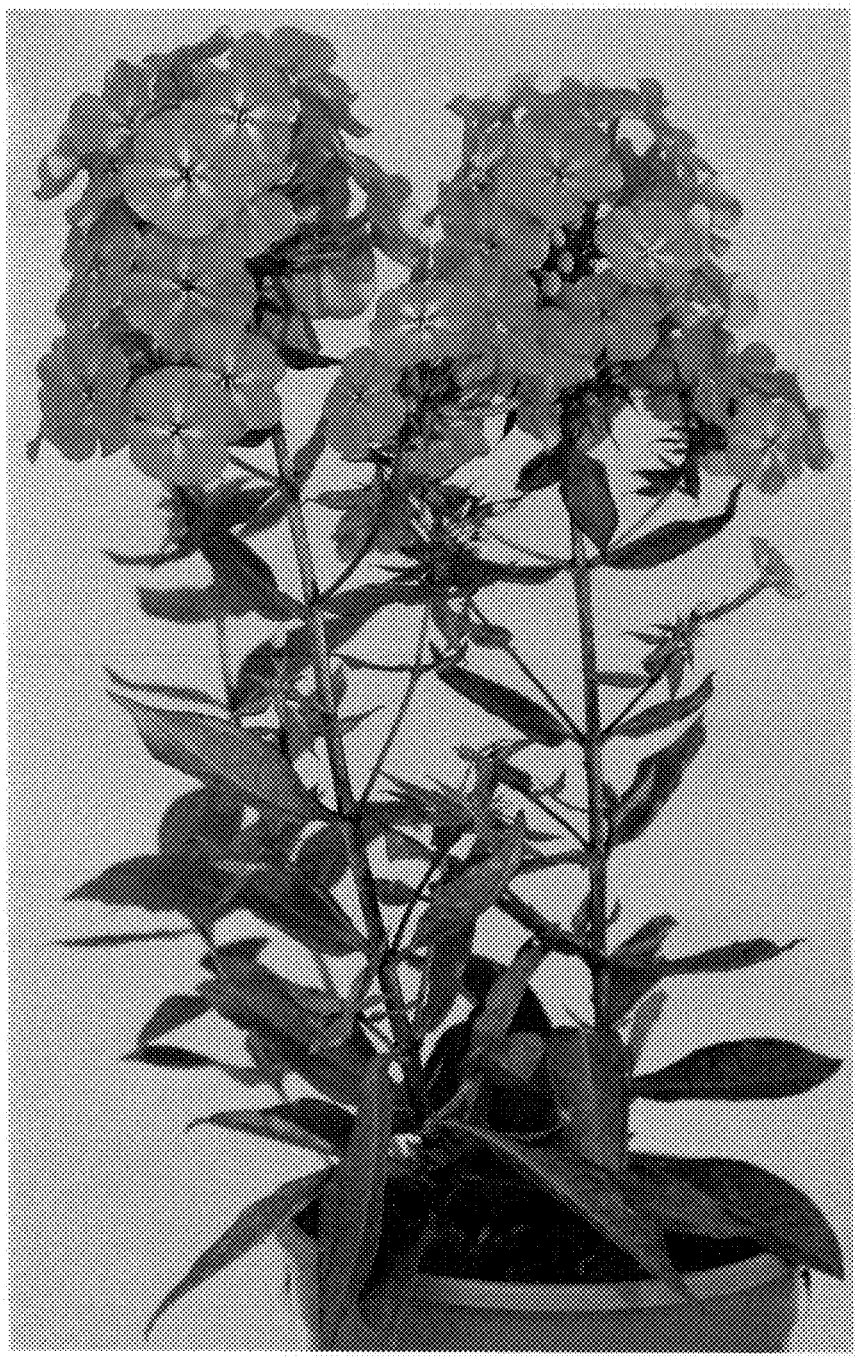

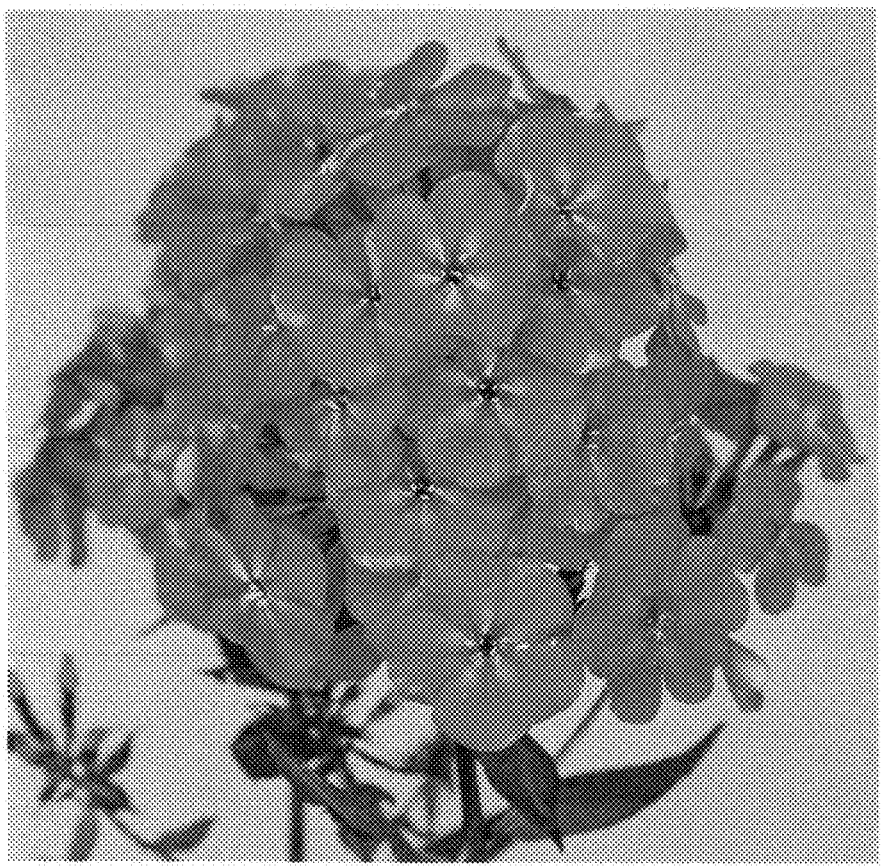

* * * * *